United States Patent
Petersen et al.

(10) Patent No.: US 9,452,146 B2
(45) Date of Patent: Sep. 27, 2016

(54) PRODUCT AND METHOD FOR IMPROVING BIOAVAILABILITY OF THERAPEUTIC COMPOUNDS

(71) Applicants: Brent L. Petersen, Twin Falls, ID (US); Melinda M. Moss, Twin Falls, ID (US); Niels J. Palmer, Twin Falls, ID (US)

(72) Inventors: Brent L. Petersen, Twin Falls, ID (US); Melinda M. Moss, Twin Falls, ID (US); Niels J. Palmer, Twin Falls, ID (US)

(73) Assignee: GLANBIA NUTRITIONALS (IRELAND) LTD., Kilkenny (IE)

( * ) Notice: Subject to any disclaimer, the term of this patent is extended or adjusted under 35 U.S.C. 154(b) by 71 days.

(21) Appl. No.: 14/217,047

(22) Filed: Mar. 17, 2014

(65) Prior Publication Data

US 2014/0275283 A1    Sep. 18, 2014

Related U.S. Application Data

(60) Provisional application No. 61/788,200, filed on Mar. 15, 2013.

(51) Int. Cl.
| | |
|---|---|
| *A61K 9/00* | (2006.01) |
| *A61K 31/00* | (2006.01) |
| *A61K 31/121* | (2006.01) |
| *A23J 3/10* | (2006.01) |
| *A23L 1/30* | (2006.01) |
| *A23L 1/305* | (2006.01) |
| *A61K 9/127* | (2006.01) |
| *A61K 9/16* | (2006.01) |

(52) U.S. Cl.
CPC ............... *A61K 31/121* (2013.01); *A23J 3/10* (2013.01); *A23L 1/3002* (2013.01); *A23L 1/3056* (2013.01); *A61K 9/1276* (2013.01); *A61K 9/1658* (2013.01); *A23V 2002/00* (2013.01)

(58) Field of Classification Search
CPC ... A61K 9/107; A61K 31/121; A61K 9/1075
USPC .......................................................... 514/679
See application file for complete search history.

(56) References Cited

U.S. PATENT DOCUMENTS

2010/0099607 A1*    4/2010 Chen ................... A61K 9/0019
                                                            514/15.1

OTHER PUBLICATIONS

Sahu et al. Fluorescence Study of the Curcumin-Casein Micelle Complexation and its Application as a Drug Nanocarrier to Cancer Cells. Biomacromolecules. 2008, vol. 9, 2905-2912.*

* cited by examiner

*Primary Examiner* — Sikarl Witherspoon
(74) *Attorney, Agent, or Firm* — Donna Russell

(57) ABSTRACT

Disclosed is a method for improving the bioavailability of a variety of compounds such as phenolic acids, polyphenols, hydroxyl-cinnamic acids, curcumin, curcumin analogs, curcuminoids, etc., using milk protein concentrate and/or similar milk protein products.

14 Claims, 1 Drawing Sheet

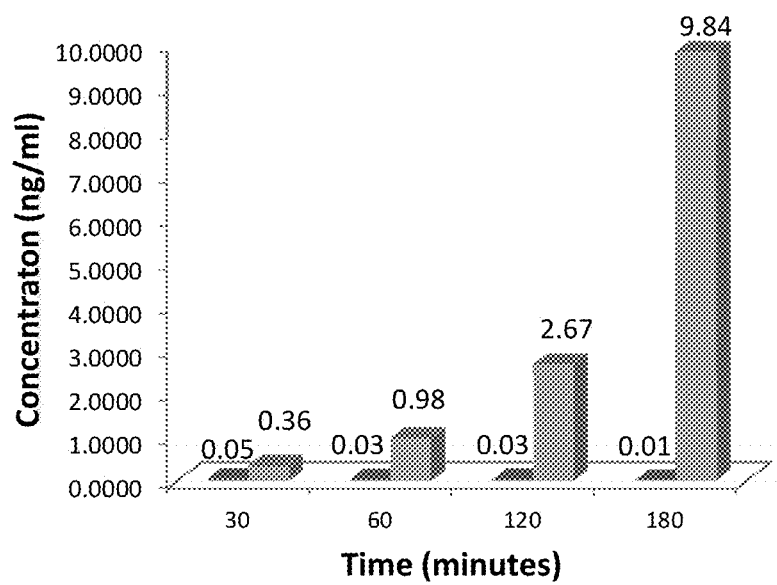

PRODUCT AND METHOD FOR IMPROVING BIOAVAILABILITY OF THERAPEUTIC COMPOUNDS

RELATED APPLICATIONS

This application claims the benefit of priority of U.S. Provisional Patent Application No. 61/788,200, filed Mar. 15, 2013. Where allowed by applicable law and/or regulation, its contents are incorporated herein by reference.

FIELD OF THE INVENTION

The present invention relates to products and methods for improving the bioavailability of therapeutic compounds using carrier compositions. More specifically, the invention relates to products and methods for improving bioavailability of compounds, such as hydrophobic phenolic compounds, for example, using casein micelles.

BACKGROUND OF THE INVENTION

Many compounds, including those from natural sources such as plant-derived compounds, do not provide their full benefit when consumed by a subject because they are not sufficiently soluble, not readily taken up by cells, easily degraded/broken down in the digestive system, etc. In other words, they are less bioavailable than are other types of compounds. One example of compounds like these is Curcumin ((1E,6E)-1,7-Bis(4-hydroxy-3-methoxyphenyl)-1,6-heptadiene-3,5-dione), a hydrophobic polyphenol derived from the *Curcuma longa* rhizome. Curcumin has been identified as the active component of turmeric, which has been used for many years for its beneficial health properties. Over the past few years, researchers have confirmed that it has provides a variety of benefits such as antioxidant, anti-inflammatory, antiviral, antibacterial, antifungal, and anticarcinogenic activities. Based upon various studies, curcumin has been suggested to have therapeutic potential for the treatment of diabetes, allergies, arthritis, Alzheimer's disease, and other chronic illnesses. One group of authors has concluded that "[c]urcumin exhibits activities similar to recently discovered tumor necrosis factor blockers (e.g., HUMIRA®, REMICADE®, and ENBREL®), a vascular endothelial cell growth factor blocker (e.g., AVASTIN®), human epidermal growth factor receptor blockers (e.g., ERBITUX®, ERLOTINIB®, and GEFTINIB®), and a HER2 blocker (e.g., HERCEPTIN®)" (Aggarwal, B. B. et al., Curcumin: the Indian solid gold. *Adv Exp Med Biol.* (2007) 595:1-75.).

In preclinical studies, curcumin has demonstrated the ability to inhibit tumor development in cell lines including, for example, oral epithelial, breast, gastric, hepatic, pancreatic, cervical, ovarian, and prostate. Some have proposed that curcumin be further developed as a cancer therapeutic because it induces apoptosis in cancer cells without inducing cytotoxic effects in healthy cells.

Curcumin is a bis-$\alpha,\beta$-unsaturated $\beta$-diketone, being predominantly keto form in acidic and neutral solutions, and taking the more stable enol form in alkaline medium. It exhibits extremely low solubility in aqueous solution ($2.99 \times 10^{-8}$ M) and limited bioavailability. For example, Wahlstrom et al. demonstrated that oral administration of 1 g/kg of curcumin resulted in minimal levels of curcumin in blood plasma of rats, leading to the conclusion that curcumin is poorly absorbed from the gut (Wahlstrom, B; Blennow, G. A study on the fate of curcumin in the rat. *Acta Pharmacol. Toxicol. (Copenhagen)* 1978, 43 (2), 86-92). Various approaches to improve curcumin solubility have included, for example, encapsulation in polymeric micelles, polymeric nanoparticles, lipid-based nanoparticles, liposomes, and hydrogels.

The "benefits of curcumin . . . are curtailed by its low oral bioavailability. Therefore, improvement of curcumin's oral bioavailability should be addressed in functional food research" (Hailong Yu and Qingrong Huang, Investigation of the Absorption Mechanism of Solubilized Curcumin Using Caco-2 Cell Monolayers, *J. Agric. Food Chem.* (2011) 59: 9120-9126). What are needed are effective methods for improving the bioavailability of curcumin and other therapeutic nutritional compositions and/or pharmaceutical compositions for which bioavailability is a limiting factor.

SUMMARY OF THE INVENTION

The invention relates to a method for producing a more bioavailable form of at least one target compound, the method comprising the steps of cooling a solution of milk protein concentrate to a temperature of from about 32 degrees Fahrenheit to about 55 degrees Fahrenheit; admixing into the solution one or more target compounds (e.g., powdered) that have been milled to a particle size of from about 0.1 µm to about 50 µm to form a target compound/milk protein concentrate solution; admixing the target compound/milk protein concentrate solution with warming; pasteurizing the target compound/milk protein concentrate solution; and spray-drying the target compound/milk protein concentrate solution. In various aspects, the target compound may be a phenolic compound. In various aspects, the milk protein concentrate may be a milk protein concentrate of at least about 80% protein. In some aspects, the milk protein concentrate may be a milk protein concentrate of at least about 85% protein. Furthermore, non-fat dry milk may be used instead of, or in conjunction with, milk protein concentrate.

In various aspects, the phenolic target compound is a phenolic acid or a polyphenol. In some aspects, the target compound may be selected from the group consisting of curcumin, synthetic curcumin, curcumin analogues, curcuminoids, curcumin complexed with at least one adjuvant molecule, and combinations thereof. In some aspects, the target compound may be selected from the group consisting of cinnamic acid, ferulic acid, caffeic acid, sinapic acid, chlorogenic acid, and combinations thereof.

The invention also relates to a method for associating one or more target compounds with casein micelles, the method comprising the steps of cooling a solution of milk protein concentrate to a temperature of from about 32 degrees Fahrenheit to about 55 degrees Fahrenheit; admixing into the solution one or more target compounds having a particle size of from about 0.1 µm to about 50 µm to form a target compound/milk protein concentrate solution; admixing the target compound/milk protein concentrate solution with warming; pasteurizing the target compound/milk protein concentrate solution; and spray-drying the target compound/milk protein concentrate solution. In various aspects, the milk protein concentrate may be a milk protein concentrate of at least about 80% protein. In some aspects, the milk protein concentrate may be a milk protein concentrate of at least about 85% protein. Furthermore, non-fat dry milk may be used instead of, or in conjunction with, milk protein concentrate. The target compound(s) may comprise a solid or liquid form, and/or may be at least one oil. In various aspects, a particle size of from about 0.1 µm to about 50 µm may be achieved by milling a solid form of the one or more target compound(s).

BRIEF DESCRIPTION OF THE DRAWINGS

FIG. 1 is a graph illustrating the difference in permeability in a Caco-2 cell model, an accepted model for the evaluation of curcumin bioavailability (Wahland, B. et al. Identification of permeability-related hurdles in oral delivery of curcumin in the Caco-2 cell model. *European Journal of Pharmaceutics and Biopharmaceutics* (2011) 77:275-282). The first bar in each pair represents the concentration, in ng/ml, at that time point for curcumin, and the second bar in each pair represents the concentration, in ng/ml, at that time point for a micelle-associated curcumin product of the invention.

DETAILED DESCRIPTION

The inventors have developed a method for associating one or more target compounds with casein micelles, improving the bioavailability of compounds which generally exhibit lower solubility and/or cellular uptake when administered via oral administration, the method comprising the steps of cooling a solution of milk protein concentrate to from about 32 degrees Fahrenheit to about 55 degrees Fahrenheit; admixing into the solution one or more target compounds having a particle size of from about 0.1 µm to about 50 µm to form a target compound/milk protein concentrate solution; admixing the target compound/milk protein concentrate solution with warming; pasteurizing the target compound/milk protein concentrate solution; and drying the target compound/milk protein concentrate solution. In various aspects, the milk protein concentrate may be a milk protein concentrate of at least about 80% protein. In some aspects, the milk protein concentrate may be a milk protein concentrate of at least about 85% protein. Furthermore, non-fat dry milk may be used instead of, or in conjunction with, milk protein concentrate. The target compound comprise a solid or liquid form, and may be in the form of an oil. In various aspects, a particle size of from about 0.1 µm to about 50 µm may be achieved by milling a solid form of the one or more target compound(s).

Often, these target compounds are compounds containing at least one phenol moiety, such as phenolic acids, polyphenols, phenyl carboxylic acids, etc. However, the method of the invention is not limited to use with phenolic compounds, and other hydrophobic compounds may also be made more bioavailable by being associated with milk-derived micelles by means of the method of the invention.

The method may also be described as a method for associating one or more target compounds with at least one casein micelle (e.g., "casein micelles") by a method comprising the steps of cooling a solution of milk protein concentrate to from about 32 degrees Fahrenheit to about 55 degrees Fahrenheit; admixing into the solution one or more target compounds having a particle size of from about 0.1 µm to about 50 µm to form a target compound/milk protein concentrate solution; admixing the target compound/milk protein concentrate solution with warming to pasteurization temperature; and drying the target compound/milk protein concentrate solution. A "target compound" may be one, or more realistically, a large number of, molecules having a similar chemical structure, these molecules having been chemically synthesized, or isolated from plants or other natural sources, for example. The molecules comprising the target compounds may also be provided in forms in which other chemical compounds, or, for example, impurities, may be present. A target compound will generally contain a significant number of molecules having a similar and desirable chemical structure. The term "comprising" will be used in this specification and in the claims, and where it is used, it should be understood that the more restrictive terms "consisting of" and "consisting essentially of" may also apply, as they fall within the broader scope of the term "comprising." Where ranges are disclosed, it should be understood by one of skill in the art that sub-ranges within, and/or including the lower and/or upper limits of those stated ranges, are contemplated as part of the invention, as well.

Milk protein concentrates are generally concentrated milk products that contain from about 40 to about 90 percent milk protein. The inventors have used milk protein concentrate 85 (MPC 85) with particularly effective results. However, those of skill in the art may also utilize milk protein concentrates of lesser protein concentrations, provided that the protein concentration is sufficient to provide effective casein micelle formation. This determination may readily be made without undue experimentation by one of skill in the art, given the disclosure provided herein by the inventors. Furthermore, non-fat dry milk may also be used in the method of the invention—either as a substitute for milk protein concentrate or in conjunction with milk protein concentrate. Solutions which the inventors have used to produce excellent results have generally been from about 5 to about 35 percent milk protein concentrate, for example.

It is desirable to produce a homogeneous, or substantially homogeneous, mixture in step (b) of the method, and exact mixing times may vary somewhat, depending upon the milk protein concentrate used, the concentration of target compound used, the equipment used, etc. Because the cooling step is intended to "open" the casein micelles so that the target compound may be incorporated into them, one of skill in the art will appreciate that holding the target compound/milk protein concentrate mixture at the chilled/lower temperature for a period of from about 1 minute to about 20 hours may be more effective for producing the desired result. An even more effective time may be from about 30 minutes to about 2 hours. Therefore, the step of "cooling" may be understood to include "cooling and holding at the target temperature for a period of time." During their research, the inventors noted that when cooling is provided by dry ice, for example, a product may be formed that is less thick and more easily pumped at lower temperatures. It is to be understood, however, that various forms of cooling known to those of skill in the art may readily be used in the method of the invention.

Milled product should be understood to contain a substantial amount of product at the desired particle size, so that a sufficient amount of target compound is available at the desired particle size to be effectively captured within micelles and minimize waste. It is not necessary that one hundred percent of the product be milled to the specified size, and in commercial use, typical milling processes generally do not produce milled product wherein more than about 90% of the product has been milled to the desired particle size.

The time interval for performing the step of admixing while warming may vary, according to the method used for warming and admixing. The step is designed to promote closing of the casein micelles that have been opened during the cooling period, and this closing process should generally take place fairly quickly, once warming has begun. Therefore, a period of a few minutes (e.g., at least about 2 minutes)

may be sufficient for step (c), and continued gentle admixing and holding at a warming temperature may also be performed, so that the period of time for step (c) may be a period of from about 2 minutes to about 12 hours, for example, keeping in mind that prolonged holding at warming temperatures may promote unwanted microbial growth.

Generally, any standard pasteurization method known to those of skill in the art may be used for the pasteurization step. For example, pasteurization may be performed by heating the mixture and holding it at 145 degrees Fahrenheit for 30 minutes, or at 161 degrees Fahrenheit for 15 seconds.

The step of drying is generally performed by a method that utilizes warming with drying, such as spray-drying, for example, which may be performed in-line, immediately after pasteurization, or the pasteurized mixture may be held for a suitable time and then spray-dried.

Milk protein concentrate (MPC) is produced from skim milk by processes that generally include steps such as ultrafiltration, diafiltration, evaporation, and spray-drying. Ultrafiltration removes lactose and minerals from skim milk, leaving behind the casein and whey proteins. Milk protein concentrate is generally considered to be made by concentrating the protein components to higher levels by the removal of non-protein components such as lactose, water, and minerals from skim milk by the ultrafiltration procedure. Generally speaking, milk protein concentrates will usually have all the fractions of milk proteins in the same ratio as they are found naturally occurring in milk. Commercially, MPCs range from about 42 percent protein (MPC 42) to about 85 percent protein (MPC 85). Lactose levels of the MPC decrease as the protein levels increase, and a diafiltration, or washing, step is usually required in order to produce a dried MPC of greater than 65 percent protein. In the method of the invention, the milk protein concentrate may be substituted with non-fat dry milk, or may be admixed with non-fat dry milk, for example, or one or more other milk products which provide a significant source of casein micelles.

Casein is the major protein component of bovine milk at about 2.8±0.3%. The casein component is a complex mixture of the four most common casein phosphoproteins $\alpha_{s1}$, $\alpha_{s2}$, $\beta$, and $\kappa$. A large proportion of casein in milk is in the form of casein micelles, each of which consist of casein molecules, calcium, inorganic phosphate and citrate ions. The casein micelle is usually thought of as a hydrated sphere, casein micelles being generally described as polydisperse, roughly spherical aggregates in milk with a mean radius of 150 nm. Their main physiological purpose is to transport calcium, proteins and phosphorus to neonates.

In 2008, Sahu et al. complexed curcumin with casein micelles, observing that curcumin molecules interact with casein micelles by binding the low-polarity regions of the casein micelles (CM). (Sahu, A. et al. Fluorescence Study of the Curcumin-Casein Micelle Complexation and its Application as a Drug Nanocarrier to Cancer Cells. *Biomacromolecules* (2008) 9(10): 2905-2912.) Under physiological buffer conditions, they also observed that their CM-curcumin complexes produce a nano-formulation that exhibited similar cytotoxic effects on HeLa cells as those of an equivalent dose of free curcumin. However, the method of Sahu et al. requires purification of casein micelles by centrifugation, re-suspension of the pellet in Tris buffer, and repetition of that process five times. The method results in the removal of whey protein. The present method does not involve centrifugation, but instead involves the use of a combination of equipment and processes that are commonly used in the dairy industry—mixers, pasteurizers, spray-dryers, etc. Also, the present method does not require that the whey protein be removed. The present method results in the formation of more complete micellular structures, while the method utilizing centrifugation and detergent re-suspension will likely produce more incomplete micelles, such as structures commonly referred to as sub-micelles. By producing micelles that are more like the natural structure found in milk, the inventors believe that they have produced a curcumin product that has better bioavailability. While various methods have been described for production of casein micelles, including micelles that are associated with curcumin, those methods generally require the use of steps such as centrifugation, addition of chemicals such as detergents, acids, etc. (Sahu, for example, uses Tris HCl), and various other steps that result in methods that may generally be more costly, time-consuming, costly, etc., than the method of the invention. The present method utilizes milk protein concentrate, non-fat dry milk, or various combinations of both, as its starting material and incorporates steps common in the dairy industry in order to produce micelle-associated target compounds, reducing costly chemical additions, centrifugation steps, etc.

The invention also relates to a micelle-associated curcumin product and/or products made by the process of the invention, the product being made by the steps of (a) cooling a solution of milk protein concentrate to from about 32 degrees Fahrenheit to about 55 degrees Fahrenheit; (b) admixing into the solution a curcumin powder that has been milled to a particle size of from about 0.1 μm to about 50 μm to form a curcumin/milk protein concentrate solution; (c) admixing the curcumin/milk protein concentrate solution with warming; (d) pasteurizing the curcumin/milk protein concentrate solution; and (e) spray-drying the curcumin/milk protein concentrate solution to product a micelle-associated curcumin product.

Products made by the method of the invention are suitable for human and/or animal consumption as food products, nutritional supplements, and/or pharmaceuticals. The method is suitable for improving the bioavailability of naturally-occurring curcumin as well as, for example, curcumin, synthetic curcumin, curcumin analogues, curcuminoids, curcumin complexed with at least one adjuvant molecule, and combinations thereof, etc. The method is also suitable for improving the bioavailability of a wide variety of other target compounds comprising phenolic compounds such as, for example, phenolic acids, polyphenols, phenyl carboxylic acids, cinnamic acids, hydroxy-cinnamic acids, flavonoids, etc. Examples of compounds which may be produced in a more bioavailable form using the method of the invention include, but are not limited to, cinnamic acid, ferulic acid, caffeic acid, sinapic acid, chlorogenic acid, and quinic acid.

Products made by the method of the invention are also suitable for administration to a human and/or animal subject for a variety of uses for which curcumin has been found to be suitable, but has not been as bioavailable as generally desired. Such uses may include, for example, acne, psoriasis, dermatitis, and rash, as well as cancer, pulmonary diseases, neurological diseases, liver diseases, metabolic diseases, autoimmune diseases, cardiovascular diseases, and immune-related chronic and/or acute diseases.

By way of example, a curcumin product can be made by making a solution of Milk Protein Concentrate 85 (MPC 85) and bringing the temperature down to 36 degrees Fahrenheit. Curcumin powder that has been milled to a particle size ranging from 0.1-50 μm is added, and once the curcumin is evenly dispersed, mixing is continued for 10 minutes and the warming of the mixture is begun. The solution/mixture is warmed to pasteurization temperature of 145 degrees Fahrenheit for 30 minutes and, after pasteurization, the resulting product is spray-dried. The powdered nature of the product lends itself to the production and sale of commercial products in powdered form, in tablets, in capsules, in suspensions or solutions, etc. Additional ingredients such as excipients, flavorings, colorings, etc., can be added, provided that they do not interfere with the target compound/micelle interaction.

Casein micelles have also been used for improving the bioavailability of non-phenolic compounds such as Vitamin D2 and Vitamin D3. Compounds incorporated into casein micelles by the method of the present invention may therefore include a variety of compounds, such as those that are less bioavailable to a human or animal because a significant amount of a compound is metabolized by intestinal bacteria, and therefore unavailable to the cells of the body. Chlorogenic acid, for example, is an ester of caffeic acid and quinic acid. Both chorogenic acid and quinic acid have been reported to have significant positive therapeutic and health benefits. However, both also have been reported to be poorly absorbed in the gut, and this has been attributed largely to the fact that a significant portion of ingested chlorogenic acid or quinic acid is metabolized by the gut bacteria, and is therefore unavailable for absorption into the cells lining the intestine (Gonthier, M-P, et al., Chlorogenic Acid Bioavailability Largely Depends on Its Metabolism by the Gut Microflora in Rats. *J. Nutr.* (2003) 133: 1853-1859). The method of the invention may produce micelle-associated chlorogenic acid and/or micelle-associated quinic acid that will be more available for absorption into the cells lining the intestine. Casein micelles are dissociated and generally broken into peptides in order to be metabolized by bacteria in the intestine, and are large enough not to be taken up into a bacterial cell. Incorporating chlorogenic acid and/or quinic acid into casein micelles may therefore shift the uptake of either compound more toward the intestinal cells of the human and/or animal, resulting in a more efficient uptake of either or both compounds.

EXAMPLES

CaCo-2 permeability of a commercially-available curcumin product and a micellar-associated curcumin of the present invention were assessed at various time points. The two samples were analyzed by LC/MS to determine curcumin concentrations in each sample. CaCo-2 cells were grown in tissue culture flasks and trypsinized, suspended in medium, and then the suspensions were applied to a CaCo-2 Millipore 96 well plate. The cells were feed at 2-day intervals and allowed to grow and differentiate for three weeks.

Samples were dissolved in transport buffer, mixed rigorously and centrifuged at 2000 rpm for 5 minutes to remove non-soluble material in the samples. The resulting supernatant was used in the assay.

The test samples were added, in a known amount, to the Apical side of the well and the amount of permeated sample was determined on the Basolateral side. The CaCo-2 cells were incubated for 30, 60, 120 and 180 minutes. In which case the receiver solution on the Basolateral side was removed and analyzed by LC/MS. To ensure properly functioning CaCo-2 cells the impermeable dye Lucifer Yellow was added on the Apical side and analyzed for on the Basolateral side. Also low and high permeability standard were used to further verify the cells. Results are shown in FIG. 1.

What is claimed is:

1. A method for producing a more bioavailable form of at least one target compound, the method comprising:
    (a) cooling a solution of milk protein concentrate to from about 32 degrees Fahrenheit to about 55 degrees Fahrenheit;
    (b) admixing into the solution one or more target compounds having a particle size of from about 0.1 µm to about 50 µm to form a target compound/milk protein concentrate solution;
    (c) admixing the target compound/milk protein concentrate solution with warming;
    (d) pasteurizing the target compound/milk protein concentrate solution; and
    (e) drying the target compound/milk protein concentrate solution.

2. The method of claim 1 wherein the milk protein concentrate comprises 85 percent protein.

3. The method of claim 1 wherein the at least one target compound is a hydrophobic compound.

4. The method of claim 1 wherein the at least one target compound is a phenolic compound.

5. The method of claim 4 wherein the at least one therapeutic target compound is a phenolic acid.

6. The method of claim 1 wherein the at least one therapeutic target compound is a flavonoid.

7. The method of claim 1 wherein the at least one therapeutic target compound is selected from the group consisting of curcumin, synthetic curcumin, curcumin analogues, curcuminoids, curcumin complexed with at least one adjuvant molecule, and combinations thereof.

8. The method of claim 1 wherein the solution of milk protein concentrate is an about 5 to an about 35 percent solution.

9. The method of claim 1 wherein a particle size of from about 0.1 µm to about 50 µm is produced by milling.

10. The method of claim 1 wherein drying the target compound/milk protein concentrate solution comprises spray-drying.

11. The method of claim 1 wherein cooling comprises cooling and holding the solution of milk protein concentrate for a period of from about 1 minute to about 20 hours at a temperature of from about 32 degrees Fahrenheit to about 55 degrees Fahrenheit.

12. The method of claim 1 wherein cooling comprises cooling and holding the solution of milk protein concentrate for a period of from about 30 minutes to about 2 hours at a temperature of from about 32 degrees Fahrenheit to about 55 degrees Fahrenheit.

13. A method for associating at least one target compound with at least one casein micelle, the method comprising:
    (a) cooling a solution of milk protein concentrate to from about 32 degrees Fahrenheit to about 55 degrees Fahrenheit;
    (b) admixing into the solution one or more target compounds having a particle size of from about 0.1 µm to about 50 µm to form a target compound/milk protein concentrate solution;
    (c) admixing the target compound/milk protein concentrate solution with warming;
    (d) pasteurizing the target compound/milk protein concentrate solution; and
    (e) drying the target compound/milk protein concentrate solution.

14. A method for making a micelle-associated curcumin product comprising:
- (a) cooling a solution of milk protein concentrate to from about 32 degrees Fahrenheit to about 55 degrees Fahrenheit;
- (b) admixing into the solution a curcumin powder that has been milled to a particle size of from about 0.1 μm to about 50 μm to form a curcumin/milk protein concentrate solution;
- (c) admixing the curcumin/milk protein concentrate solution with warming;
- (d) pasteurizing the curcumin/milk protein concentrate solution; and
- (e) spray-drying the curcumin/milk protein concentrate solution to product a micelle-associated curcumin product.

* * * * *